US012428617B2

(12) United States Patent
Pohl et al.

(10) Patent No.: US 12,428,617 B2
(45) Date of Patent: Sep. 30, 2025

(54) DISPOSABLE DEVICE FOR VENTING A SEALED CONTAINER AND ALIQUOTING THEREFROM

(71) Applicant: BD KIESTRA B.V., Drachten (NL)

(72) Inventors: Brent Ronald Pohl, Timonium, MD (US); Franciscus Hermannus Feijen, Leeuwarden (NL); Robert Edward Armstrong, Hunt Valley, MD (US); Ammon David Lentz, York, PA (US)

(73) Assignee: BD KIESTRA B.V., Drachten (NL)

( * ) Notice: Subject to any disclaimer, the term of this patent is extended or adjusted under 35 U.S.C. 154(b) by 0 days.

(21) Appl. No.: 17/632,597

(22) PCT Filed: Aug. 5, 2020

(86) PCT No.: PCT/US2020/045030
§ 371 (c)(1),
(2) Date: Feb. 3, 2022

(87) PCT Pub. No.: WO2021/026249
PCT Pub. Date: Feb. 11, 2021

(65) Prior Publication Data
US 2022/0290089 A1    Sep. 15, 2022

Related U.S. Application Data

(60) Provisional application No. 62/907,060, filed on Sep. 27, 2019, provisional application No. 62/883,427, filed on Aug. 6, 2019.

(51) Int. Cl.
*C12M 1/26* (2006.01)
*B01L 3/00* (2006.01)

(52) U.S. Cl.
CPC .......... *C12M 33/04* (2013.01); *B01L 3/5635* (2013.01); *B01L 2200/026* (2013.01);
(Continued)

(58) Field of Classification Search
CPC .................. C12M 33/04; B01L 3/5635; B01L 2200/0684; B01L 2200/141;
(Continued)

(56) References Cited

U.S. PATENT DOCUMENTS 3,941,171 A    3/1976  Ogle
4,505,709 A    3/1985  Froning et al.
(Continued)

FOREIGN PATENT DOCUMENTS

CN    104107054 A    10/2014
CN    104673661 A    6/2015
(Continued)

OTHER PUBLICATIONS

Translation of WO9808436A1, Tavernier Laurent, Mar. 5, 1998 (Year: 1998).*
(Continued)

*Primary Examiner* — Henry H Nguyen
(74) *Attorney, Agent, or Firm* — Botos Churchill IP Law LLP

(57) ABSTRACT

A multi-port disposable device that can both vent a sealed culture vessel and draw a sample therefrom into a collection vessel. The multi-port disposable device has a first port configured to receive the top portion of a culture vessel and attach thereto. The multi-port disposable device has a second port configured to receive a sample collection vessel. The multi-port disposable device has first and second needles. The first needle has a cannula configured to penetrate a septum or cap of the culture vessel. Optionally, the cannula terminates in a layer of foam that carries a microbial agent such that any vapor that is transmitted from the culture vessel through the cannula when venting the sealed culture vessel is absorbed by the foam. Optionally, the ports of the disposable device are configured as sleeves. The sleeve of
(Continued)

the first port receives a portion of the culture vessel and the sleeve of the second port receives the collection vessel. The second needle has a cannula that penetrates both the septum or cap of the culture vessel and the septum or cap of the collection vessel, when the culture vessel and the collection vessel are brought into the device, thereby providing for fluid communication between the culture vessel and the collection vessel. The second cannula provides the flow pathway for delivering sample from the culture vessel to the collection vessel.

11 Claims, 17 Drawing Sheets

(52) U.S. Cl.
CPC . *B01L 2200/0684* (2013.01); *B01L 2200/141* (2013.01); *B01L 2300/0672* (2013.01)

(58) Field of Classification Search
CPC ....... B01L 2300/0672; B01L 2300/042; B01L 2400/049
See application file for complete search history.

(56) References Cited

U.S. PATENT DOCUMENTS

| | | | |
|---|---|---|---|
| 4,684,365 | A | 8/1987 | Reinicke |
| 4,697,622 | A | 10/1987 | Swift et al. |
| 5,049,129 | A | 9/1991 | Zdeb et al. |
| 5,653,686 | A | 8/1997 | Coulter et al. |
| 6,355,023 | B1* | 3/2002 | Roth ................ A61B 5/150389 604/905 |
| 6,579,245 | B1 | 6/2003 | Pakszys |
| 2002/0185457 | A1 | 12/2002 | Smith et al. |
| 2006/0184103 | A1* | 8/2006 | Paproski ............... A61J 1/2096 604/86 |
| 2007/0178018 | A1* | 8/2007 | Virno .................... B01L 3/5021 435/283.1 |
| 2008/0199900 | A1 | 8/2008 | Signore et al. |
| 2011/0030845 | A1 | 2/2011 | Chong et al. |
| 2011/0168294 | A1* | 7/2011 | Jakobsen .............. A61J 1/2096 141/65 |
| 2011/0212517 | A1* | 9/2011 | Dahm ................... B01J 19/249 435/306.1 |
| 2013/0197466 | A1* | 8/2013 | Anitua Aldecoa .......................... A61B 5/150351 604/405 |
| 2014/0238950 | A1* | 8/2014 | Jackson ............... B65D 51/225 215/247 |
| 2015/0123398 | A1* | 5/2015 | Sanders .............. F16L 37/0841 285/330 |
| 2016/0008808 | A1* | 1/2016 | Levine ................. A61M 1/029 422/522 |
| 2016/0024450 | A1* | 1/2016 | Quick .................... C12M 21/08 435/379 |
| 2018/0296748 | A1 | 10/2018 | Emerson |

FOREIGN PATENT DOCUMENTS

| | | | |
|---|---|---|---|
| CN | 213085975 U | 4/2021 | |
| JP | S63503366 A | 12/1988 | |
| WO | 8707159 A1 | 12/1987 | |
| WO | WO-9808436 A1 * | 3/1998 | ............. A61B 5/097 |
| WO | 2008039686 A2 | 4/2008 | |

OTHER PUBLICATIONS

International Search Report and Written Opinion for Application No. PCT/US2020/045030 dated Nov. 17, 2020.
Extended European Search Report issued in corresponding EP application No. 20849788.3 on Jun. 21, 2023., pp. 11.
First Examination Report issued in corresponding Indian application No. 202217011222 on Aug. 23, 2024., pp. 7.
Office Action issued in corresponding Japanese Application No. 2022-507551 on Jul. 26, 2024., pp. 7.
First Office Action issued in corresponding CN application No. 2020800540022 on Jan. 25, 2025, pp. 22.
Japanese Office Action issued in JP application No. 2022-507551 on Mar. 4, 2025, pp. 8.
Office Action issued in Australian Patent Application No. 2020325201 on Feb. 25, 2025 (3 pp.).
Hearing Notice issued in corresponding Indian Application No. 202217011222 on May 6, 2025, p. 3.
Office Action issued in corresponding Mexican Application No. MX/a/2022/001582 on Apr. 1, 2025., p. 8.

* cited by examiner

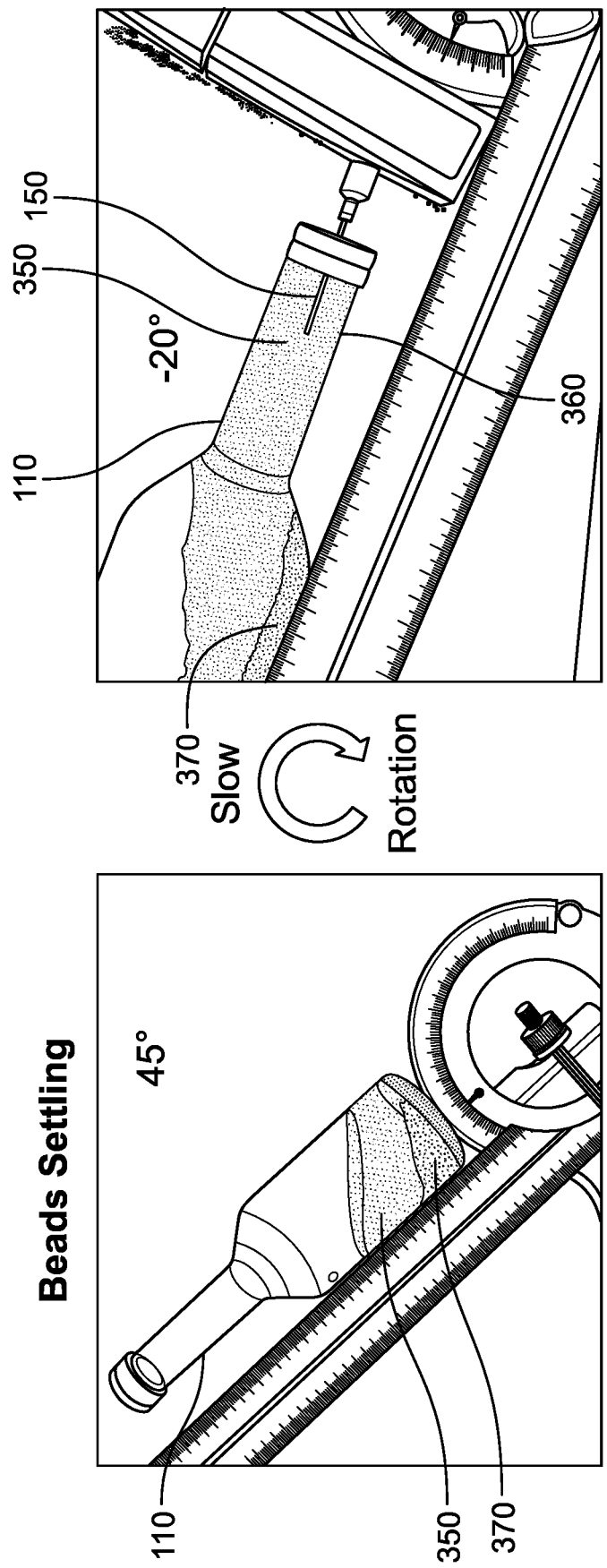

Incline Angle

BACTEC Plus (-10mL)

9.5°

12.5°

20°

Sprotte

Whitacre

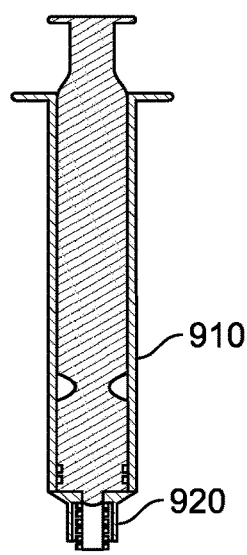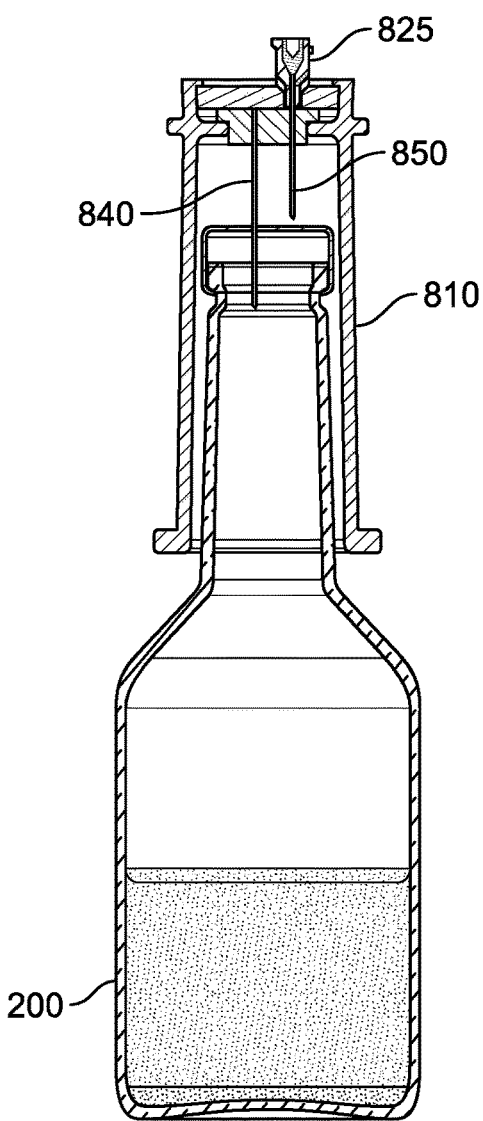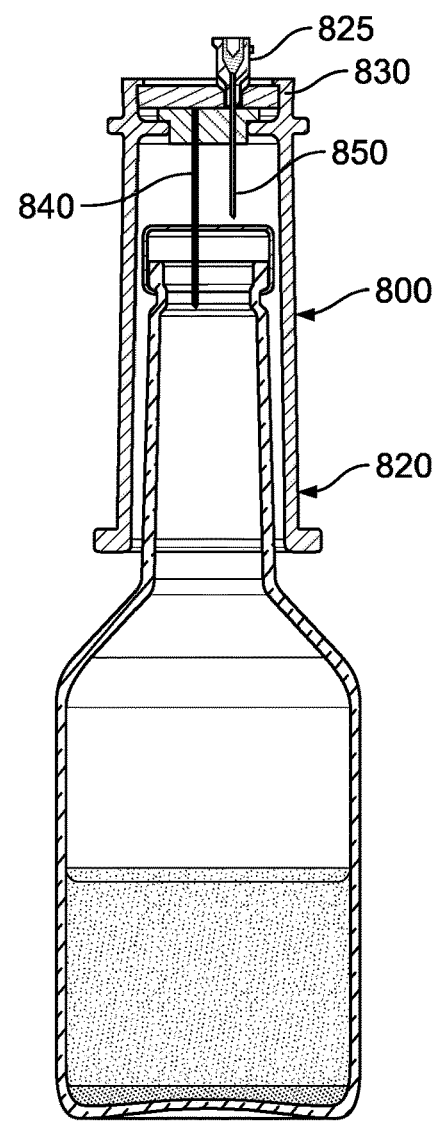
FIG. 27B　　　　　　FIG. 27C

DISPOSABLE DEVICE FOR VENTING A SEALED CONTAINER AND ALIQUOTING THEREFROM

CROSS REFERENCE TO RELATED APPLICATION

The present application is a national phase entry under 35 U.S.C. § 371 of International Application No. PCT/US2020/045030, filed Aug. 5, 2020, published in English, which claims the benefit of the filing date of U.S. Provisional Application No. 62/883,427 which was filed on Aug. 6, 2019 and also the benefit of the filing date of U.S. Provisional Application No. 62/907,060, which was filed Sep. 27, 2019, the disclosures of which are incorporated by reference herein.

TECHNICAL FIELD

The invention described herein is directed to a dual port disposable device having a venting needle and a separate fluid transfer needle for both venting a culture vessel and obtaining an aliquot of sample from the culture vessel.

BACKGROUND

Various embodiments of the present disclosure describe systems and methods for testing samples (e.g., biological samples, environmental samples, food samples etc.) for microbial contamination. Samples inoculated into culture vessels will cause the conditions in the culture vessel to change over time if such samples are contaminated with microorganisms. The metabolic activity of microorganisms, if present in the sample, changes the gas composition, the gas pressure and/or the pH in the culture vessel. Because the internal gas pressure in the culture vessel increases over time (if microorganisms are present in the sample), the contents of the culture vessel cannot be accessed without venting the gases from the culture vessel before the contents of the culture vessel are drawn therefrom. Therefore, there is a need for a device that can both safely vent a culture vessel and allow an aliquot of the sample in the culture vessel to be obtained.

Detecting a positive blood culture (PBC) is just the beginning of a long series of processes to determine the identification of microorganisms in the culture vessel, and the proper drug treatment for the patient infected with that microorganism. The first step is getting the microorganism out of the bottle and into a suitable collection container for downstream processing by identification and antibiotic susceptibility instrumentation.

In a blood culture container, such as the BD BACTEC™ bottle (BACTEC is a trademark of Becton Dickinson and Co.), bacteria growth produces carbon dioxide (or other gases such as $CO_2$ depending on the type of microorganism in the sample). Regardless, the production of these gases by the microorganisms causes a slight increase in the internal pressure of the culture vessel. Penetration of the bottle septum must be performed in a way to eliminate or contain the aerosolized bacteria media. This will prevent contamination of the internal instrument surfaces and potential sample cross-contamination. Accessing the contents of the blood culture container in a manner that does not permit the contents of the culture bottle to escape into the surrounding environment is of paramount importance. Solutions to this problem continue to be sought.

BRIEF SUMMARY

In a microbiological laboratory setting inoculated blood culture bottles are incubated to detect bacteria growth. For positive blood cultures, an aliquot is taken from the bottle for downstream identification and susceptibility testing. The disposable apparatus described herein is used during the aliquot stage of processing the blood culture. The disposable apparatus has a housing having disposed therein at least two needles having different lengths. The disposable apparatus has two opposed receptacles (also referred to herein as ports or sleeves). One receptacle is configured to attach to blood culture vessel such as a blood culture bottle. The longer needle of the disposable apparatus punctures the culture bottle septum first. Pressurized gases, if any, escape through a venting needle and aerosols are captured in a thick layer of open cell foam containing an antibacterial agent. During venting, the assembly of the disposable apparatus and the blood culture vessel are in an approximately upright position so that the gases escape upward.

Optionally, after venting, the assembly of the dual port disposable apparatus and the blood culture vessel is at least somewhat inverted so that the disposable apparatus is held lower than the blood culture bottle and the liquid contents of the blood culture are in fluid communication with the needles of the disposable apparatus. Optionally, after venting, the blood culture vessel remains in an upright position for aliquoting. A sealed and sterile collection vessel is inserted into the second sleeve of the second port in the dual port disposable apparatus such that the collection vessel seal is punctured by the second needle. The vacuum of the collection vessel draws an aliquot of the blood culture into the sterile collection vessel from the culture vessel.

For example, some embodiments describe a dual port disposable device with a means to penetrate a septum or cap of a culture vessel and permit gaseous discharge of the culture vessel prior to obtaining an aliquot of the sample. This allows for pressure relief of the culture vessel interior prior to retrieving an aliquot of the contents of the culture vessel. In some embodiments, the gases in the headspace of the culture vessel can exit the dual port disposable device without contaminating the environment outside the assembly or allowing sample contamination.

In some embodiments, the dual port disposable device includes a membrane to prevent liquid carried by the discharged vapor from escaping the dual port disposable device. The dual port disposable device is also used draw an aliquot of the sample from the culture vessel (typically mixed with culture medium) into a collection vessel for sub culturing or aliquoting for another diagnostic process such as molecular diagnostics.

One example of the dual port disposable device describe herein has a first port configured to receive the top portion of a culture vessel and attach thereto. The dual port disposable device has a second port configured to receive a sample collection vessel. The dual port disposable device has a cannula configured to penetrate a septum or cap of the culture vessel. The cannula terminates in a layer of foam that carries an anti-microbial agent such that any vapor that is transmitted from the culture vessel through the cannula is absorbed by the foam and neutralized. Optionally, the ports of the disposable device are configured as sleeves. The sleeve of the first port receives a portion of the culture vessel and the sleeve of the second port receives the collection vessel. A second cannula penetrates both the septum or cap of the culture vessel and the septum or cap of the collection vessel, providing for fluid communication between the culture vessel and the collection vessel. The second cannula provides the flow pathway for delivering sample from the culture vessel to the collection vessel. The first cannula provides a flow pathway for air to enter the culture vessel as sample is delivered to the collection vessel.

Optionally, the collection vessel is a syringe. In this embodiment the second cannula terminates at the syringe. The syringe draws the sample from the culture vessel for delivery into the collection vessel. Optionally, the second cannula terminates with a connector, such as a luer lock connector through which the syringe is connected to the disposable device, thereby providing the vacuum source sufficient to draw the desired aliquot from the culture vessel. Such a connector also permits the syringe to be disconnected from the device.

BRIEF DESCRIPTION OF DRAWINGS

FIGS. 10A and 10B illustrate the response of the contents of the blood culture bottle at an upward 45-degree angle and a downward 20-degree angle (both from horizontal);

FIGS. 27A-C illustrates the embodiment of FIG. 26 with a luer connector for the syringe.

DETAILED DESCRIPTION

Figure 1:
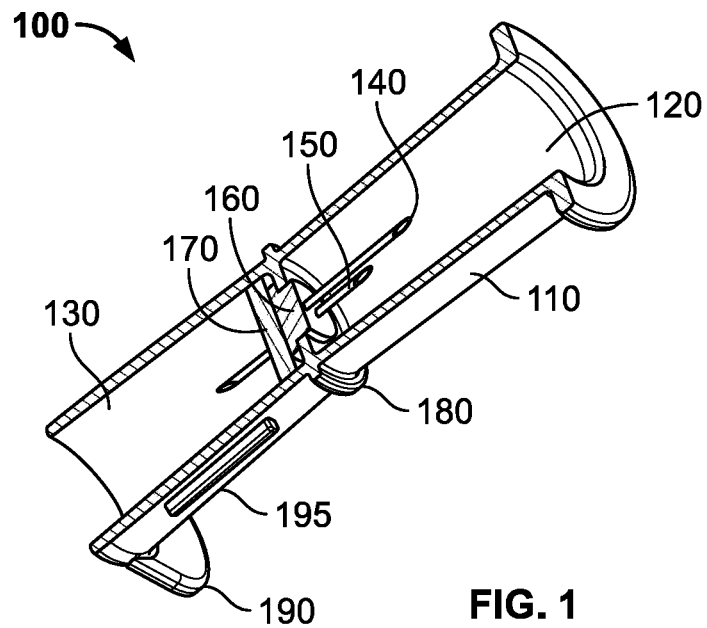
FIG. 1 is a cutaway view of disposable apparatus.

FIG. 1 is a cutaway view of a dual port disposable device according to one embodiment of the present invention. The device 100, has a housing 110 that consists of a first port 120 and a second port 130. Optionally, the housing 110 is a unitarily molded body. First and second ports 120 and 130 are configured as sleeves. The dual port disposable device 100 has a first needle 140, that is a venting needle and a second needle 150 that is the aliquoting needle. Both needles are held in the housing 110 by a needle retaining insert 160 (needle insert herein) that separates the first port 120 from the second port 130. The needle retaining insert is secured by a flange 161 formed at the respective distal ends of the first port 120 and the second port. Flange 161 also prevents the vessels advanced into first and second ports from over advancing into the adjacent port. Optionally, the dual port disposable device 100 also has disposable antimicrobial foam 170 located at the distal end of the second port 130 and adjacent the needle insert 160. Both needles pass through the needle insert 160. The venting needle 140 terminates in the antimicrobial disposable foam 170. The aliquoting needle passes through the antimicrobial foam layer 170.

Optionally, the dual port disposable device has external features on the molded housing 110 to facilitate automating the gripping and handling of the dual port disposable device. Examples of such features are illustrated in FIG. 1. Illustrated are a gripper centering rib 180 and an anti-rotation ring 190 and key 195.

Figure 2:
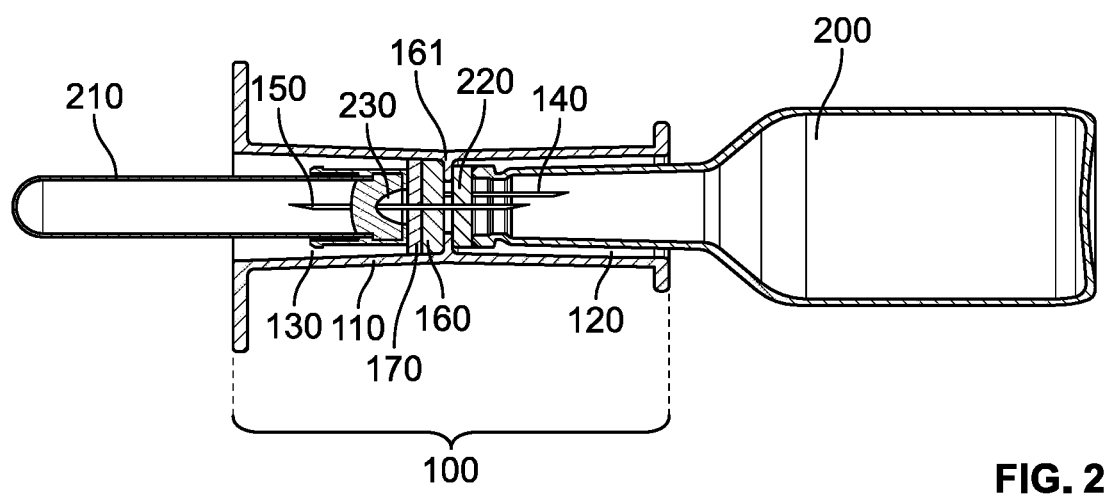
FIG. 2 is a cutaway view of the disposable apparatus of FIG. 1 assembled to a blood culture vessel.

Referring to FIG. 2, an assembly of the dual port disposable device 100 described in FIG. 1 is illustrated as assembled with a culture bottle 200 and a collection tube 210. The venting needle 140 is placed in the dual port disposable device 110 such that it only pierces the cap 220 of the culture bottle 200 and does not pierce the septum 230 of the collection tube 210. The aliquoting needle 150 pierces both the cap 220 of the culture bottle 200 and the septum 230 of the collection tube 210. The culture bottle 200 is received into the sleeve of the first port 120 and the collection tube 210 is received in the second port 130. The first and second ports 120, 130 are formed as sleeves in the unitary housing 110 of the dual port disposable device 100. As noted in the description of FIG. 1, venting needle 140 and aliquoting needle 150 are held in the dual port disposable device by the needle insert 160. The antimicrobial disposable foam 170 is placed at the distal end of the second port 130 adjacent the retaining insert. Optionally, the antimicrobial foam could be place at the distal end of the first port 120.

The dual port disposable device addresses the problem of aerosolization. As explained previously, bacteria growth in a blood culture bottle produces a gas such as carbon dioxide or oxygen (depending upon the type of bacteria) that results in a slightly pressurized bottle. Penetrating the culture bottle septum must be performed in a way to eliminate or contain the aerosolized bacteria and media to prevent contamination of inside instrument surfaces. The dual port disposable device addresses this problem by inserting the antimicrobial infused disposable foam on the vented side of the venting needle so that any aerosolized bacteria and media are trapped in the foam and do not enter the environment surrounding the dual port disposable device.

The dual port disposable device addresses the problem of contamination. As noted above, if the aerosol carries bacteria from the venting site to the surrounding environment there is a risk of microbial contamination as described above. The aerosol-trapping foam minimizes and even eliminates the deposit of microbial contamination on the surfaces of the culture vessel and the collection vessel. The aerosol-trapping foam also reduces or eliminates contaminants from entering the culture vessel during venting. This allows the sample remaining in the culture bottle to be aliquoted from the culture vessel even after the initial sample is acquired.

The dual port disposable device facilitates automation by having features such as the gripper centering rib 180 and an anti-rotation ring 190 and key 195 described above. These features facilitate the use of automation equipment to reliably remove the dual port disposable device from its packaging, grip and manipulate the dual port disposable device to vent and aliquot from the culture vessel and dispose of the dual port disposable device.

The dual port disposable device is provided with needles that do not "core" the septum septum/stopper of the culture vessel/collection vessel. Coring results when a piercing device leaves a permanent channel through a septum/stopper. Any piercing of the septum/stopper that tears or otherwise damages the septum or stopper could lead to leakage and must be avoided.

Culture medium often contains particles in addition to nutrients. For example, Bactec™ Plus media contains beaded resin for antibiotic neutralization. The needles for the dual port disposable device have cannulas with a diameter that will prevent beaded resin from being drawn into the collection vessel along with the sample.

Needle safety is of concern, even in automated systems. Optionally, the dual port disposable device will minimize the instances in which a technician will encounter an exposed sharp.

Figure 3:
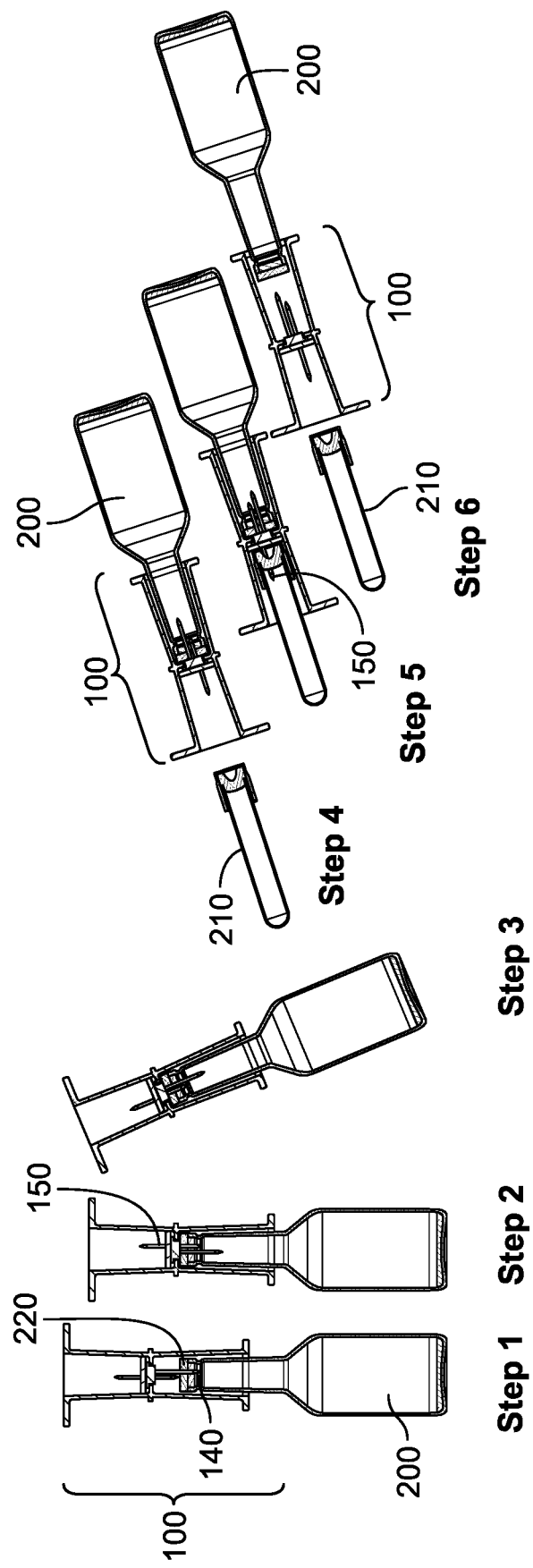
FIG. 3 illustrates the orientation of the assembly of FIG. 2 during venting and aliquoting.

To ensure that an adequate aliquot of the sample is drawn into the collection vessel, the dual port disposable device 100 is assembled to the culture vessel 200 and the collection vessel in the manner illustrated in FIG. 3. In step 1, the dual port disposable device 100 is assembled to the culture vessel 200. The vent needle 140 is inserted through the cap 220 of the culture bottle. After venting, in step 2, the dual port disposable device 100 is advanced further down onto the culture vessel 200 such that the aliquot needle 150 pierces the cap 220 of the culture bottle. In step 3, the assembly of the dual port disposable device 100 and the culture vessel 200 is rotated/rocked to cause the beads in the culture medium/sample to settle to the bottom of the culture bottle 200. After this, the assembly of the dual port disposable device 100 and the culture vessel 200 is positioned at a negative angle relative to horizontal as illustrated in step 4. In step 5, the collection vessel 210 is inserted into the second port 130 of the dual port disposable device 110 such that the aliquot needle 150 pierces the septum 230 of the collection vessel 210. The assembly of the collection vessel 210, dual port disposable device 100 and the culture vessel 200 is held at a negative angle during sample collection after which, in step 6, the collection vessel 210 is removed from the assembly. In step 7, the culture bottle 200 is removed from the dual port disposable device and the dual port disposable device is discarded.

Figure 4:
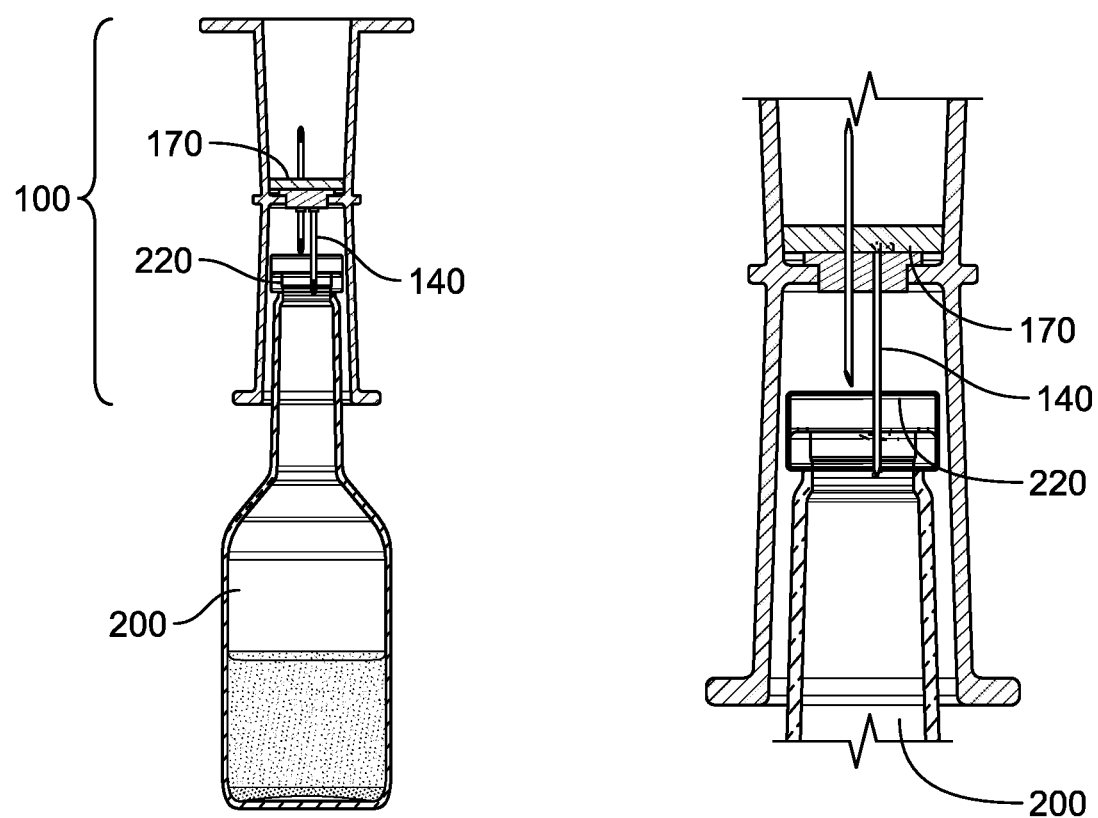
FIG. 4 illustrates the position of the disposable apparatus of FIG. 1 relative to the blood culture bottle to which it is assembled during venting.

FIG. 4 illustrates how the dual port disposable device is advanced into contact with the culture vessel 200 to perform a first venting step and then positioned for a second aliquoting step. In the first venting step, only the first venting needle 140 pierces the cap 220 of the culture vessel 200. The distal end of the venting needle 140 is embedded in the disposable antimicrobial foam 170 such that any aerosol emitted as a result of venting the culture vessel 200 is trapped by the antimicrobial foam, thereby reducing/eliminating the risk of contamination by venting. Since the venting needle extends further into the first port 120 than the aliquot needle, the culture vessel 200 is vented as the dual port disposable device is further advanced into initial engagement with the culture vessel. The aliquot needle 150 does not pierce the cap 220 of the culture vessel until the collection vessel 210 is inserted into the second port 130, which forces the aliquoting needle to pierce the cap 220 of the culture vessel.

In an automated method, a robotic gripper (not shown) will acquire the dual port disposable device 100 and locate the first port 120 concentrically with the top of an upright culture vessel 200. The dual port disposable device 100 translates in the z-axis such that the venting needle 140 contacts and penetrates the cap of the culture vessel. Simultaneously with the puncture of the cap 220 by the venting needle 140, pressurized gases, if any, escape through the venting needle 140 and aerosol is captured on a suitably thick layer of open cell foam preferably containing an antibacterial agent (i.e. disposable antimicrobial foam 170).

Figure 5:
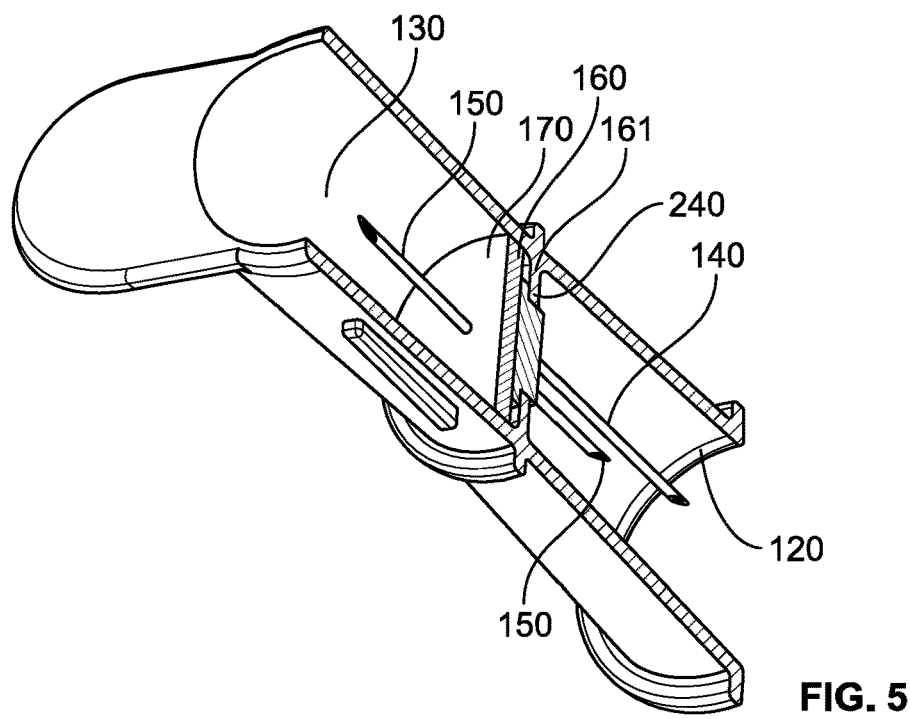
FIG. 5 is a portion of the disposable apparatus of FIG. 1, illustrating the two needles and the antimicrobial foam.

FIG. 5 is a detail view of the portion of the dual port disposable device 100 in which the disposable antimicrobial foam 170 is positioned at the distal end of the second port 130. The needle insert 160 is positioned at the distal end of the first port 120. A layer of foam saturated with antibacterial agent comes into compression contact with the closure at the top of the collection vessel (for example a Becton Dickinson BD reclosing septum cap or vacutainer). The automated apparatus could rotate the housing 110 such that the disposable antimicrobial foam layer 170 could radially wipe the top surface of the needle insert 160 before the needles 140 and 150 are removed from, respectively, the culture vessel and the collection vessel. FIG. 5 also illustrates that the interior of the housing 110 has a flange 240 through which a narrower diameter portion 250 of the needle insert 160 extends. The wider diameter portion 260 of the needle insert 160 rests on the flange 240 to secure the needle insert in the housing 100 and providing a seal between the first port 120 and the second port 130.

Figure 6:
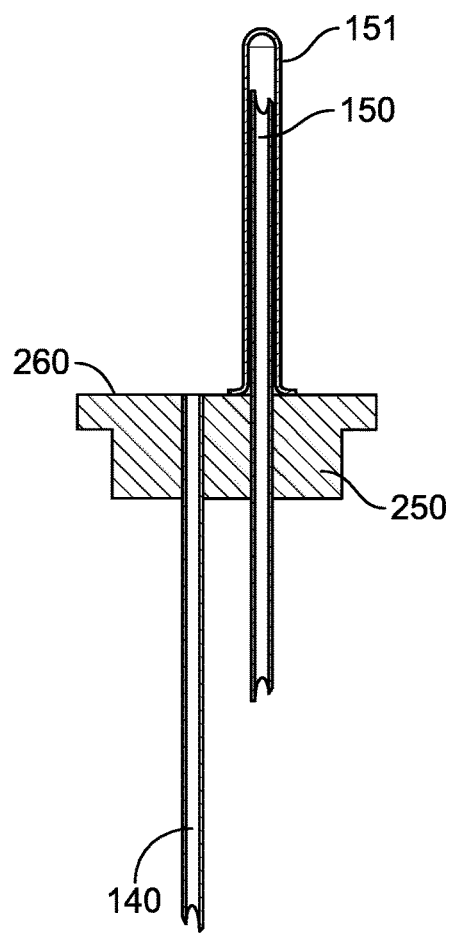
FIG. 6 is a cutaway side view of the two needles passing through the retaining insert.
Figure 7:
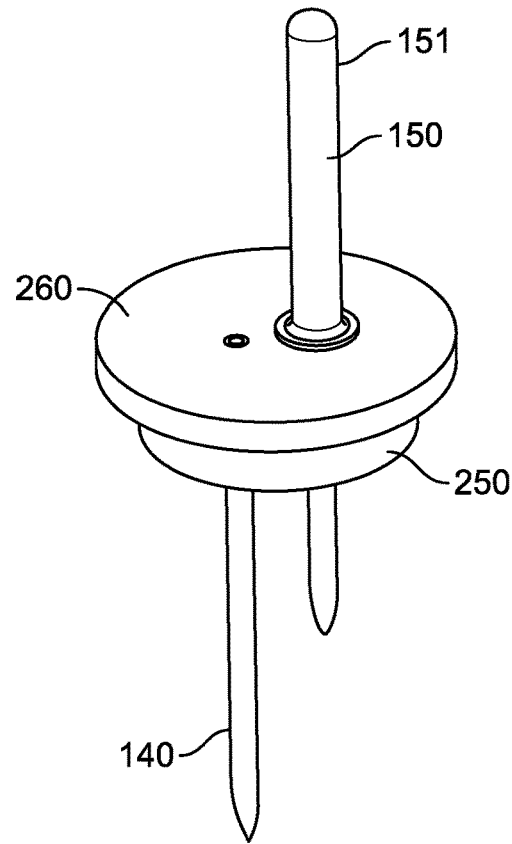
FIG. 7 is a perspective view of the two needles passing through the retaining insert.

FIG. 6 is a detail cut away view of the needle insert 160. FIG. 6 illustrates the wider diameter portion 260 of the needle insert 160 that rests on the flange 240 (FIG. 5) to secure the needle insert 160 in the housing 110 thereby providing a seal between the first port 120 and the second port 130. Aliquoting needle 150 has a sheath 151 thereon. The sheath seals the aliquoting needle when the disposable device is secured to the culture vessel. The sheath prevents the contents of the culture vessel from flowing out of the culture vessel prior to attachment of the collection vessel to the disposable device. One example of a suitable material for the needle insert 160 is butyl rubber. The optional sheath placed over one or more of the needles to avoid contamination can also be made of butyl rubber. Alternatively, a thick layer of foam covering needle could be implemented that would perform a cleaning operation to the top of the Bactec™ bottle, before compressing the foam cylinder and needle piercing the septum. FIG. 7 illustrates the same needle insert of FIG. 6 but in perspective view.

Figure 8:
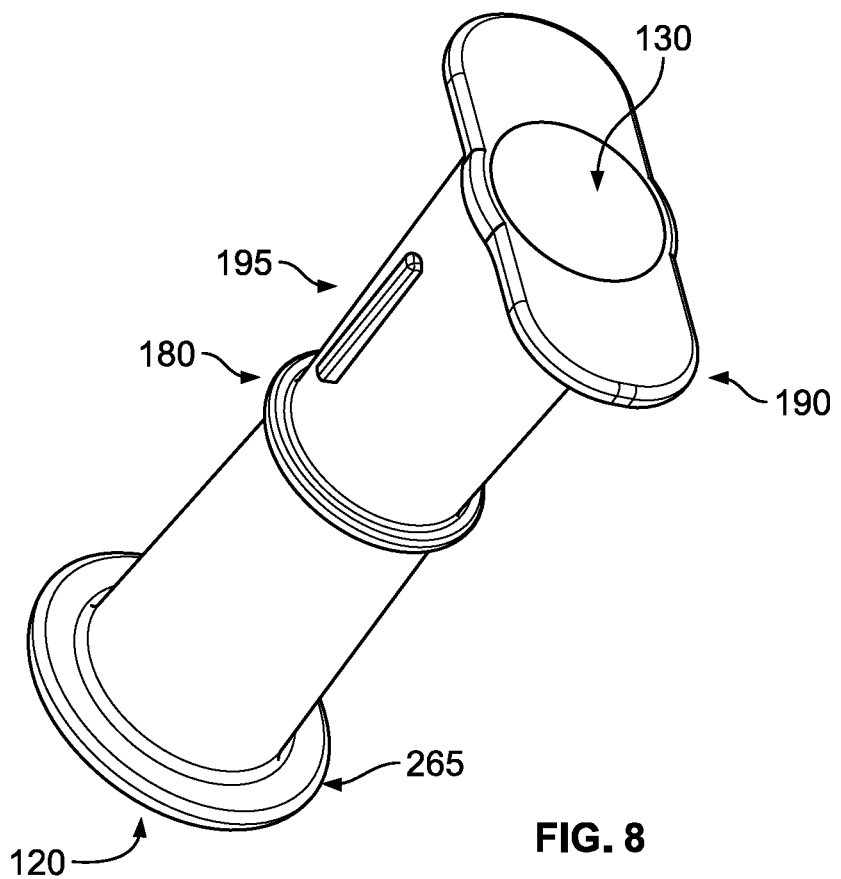
FIG. 8 illustrates the housing for the disposable apparatus.

FIG. 8 illustrates the housing 110. As illustrated the housing has a first flange 265 which is at the proximal end of the first port 120 and a second flange 190 (i.e. the anti-rotation ring) that is at the proximal end of the second port 130. The flange 265 is symmetric and the second flange 190 is asymmetric. The asymmetric flange 190 has two portions formed adjacent opposite sides of the proximate end of the second port 130. The asymmetric flange 190 can be received by and locked into engagement with an automated instrument that will position the device 100 on a blood culture vessel. The gripper centering rib 180 allows the jaw of a gripping mechanism to grip in the same axial location on the dual port disposable device for each aliquot of sample obtained using the device.

External radial key feature 195 also works collaboratively with the gripper geometry to ensure the dual port disposable device 100 is picked up in the same radial orientation. This provides predictable insertion of the venting needle in the bottle along at the same radial angle for each sample.

Figure 9:
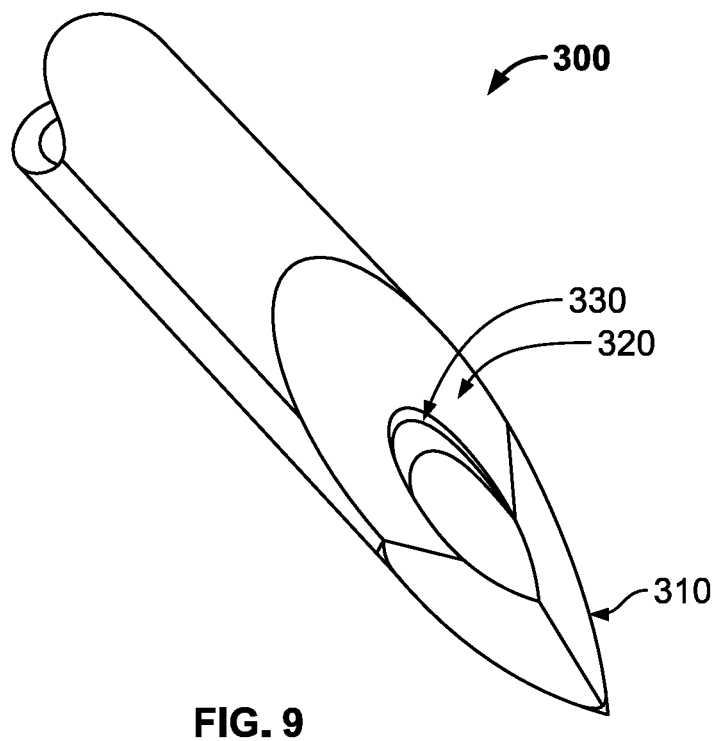
FIG. 9 illustrates one embodiment of a venting needle.

As noted above, optionally the needles do not cause coring of the septum that the needle pierces. One skilled in the art is aware of strategies in both needle and septum design that reduce the instances in which the septum is cored. One example of a needle 300 designed to control or reduce the instance of coring is illustrated in FIG. 9. The needle 300 has a first bevel 310, a second bevel 320 and heel feature 330. To reduce coring, the heel feature 330 is bead blasted to dull its edge, which promotes displacement of the septum material rather than cutting the septum material.

The cap 220 is made of conventional septum materials such as brominated or chlorinated butyl rubber. Typically, such materials have a durometer Shore A hardness of about 40 to about 50. Such materials can also be used for the stopper 230 for the collection tube 210. Materials with lower durometer values are less likely to core (or be cored). Lubricants such as silicone and Teflon are optionally used on the exterior of the needle to reduce puncture force, promote ease of insertion and reduce likelihood of coring and tearing. Abrading the heel of the bevel to address these problems is also contemplated to ensure that the needle does not core the septum.

One potential issue with drawing sample from the culture vessel is that there is resin in the media which can clog the needle. Solutions to this problem include needles with wider diameter cannula and ensuring that the needle opening is sufficiently sized to either prevent the resin from entering the cannula or sufficiently small so that the resin does not enter the cannula.

Figure 11A:
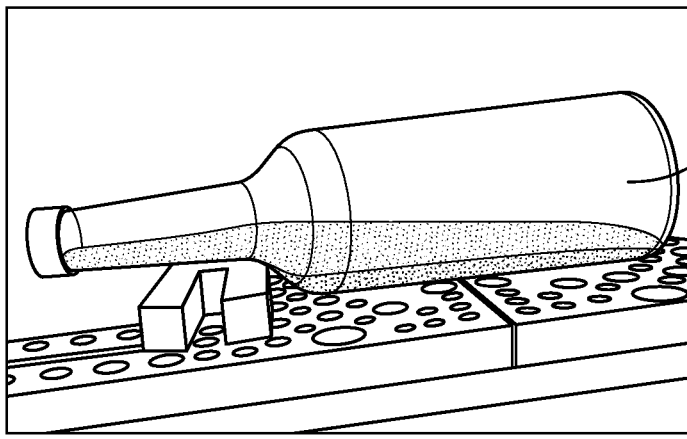
FIGS. 11A-11C illustrate the response of the contents of the blood culture bottle at decline angles of 9.5 degrees, 12.5 degrees and 20 degrees from horizontal.
Figure 11B:
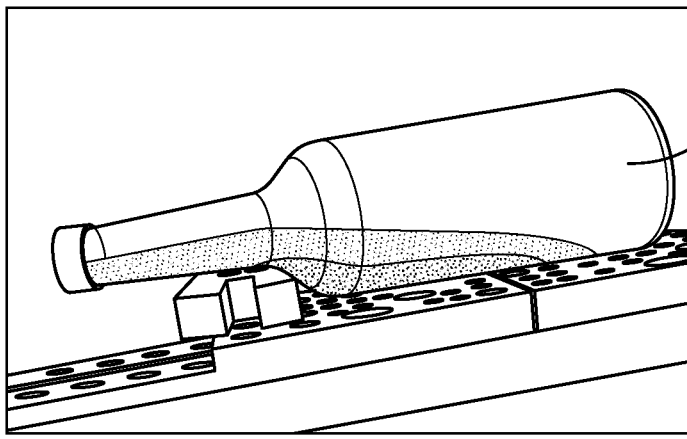
Figure 11C:
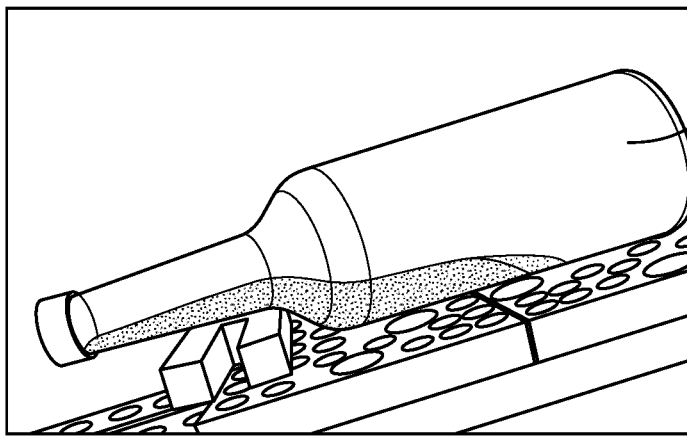

FIGS. 10A and 10B illustrate a process of positioning bottle 110 first at a 45°-degree upward angle that produces a relatively bead-free suspension 350 (FIG. 10A). The bottle is then rotated to an approximately 20° downward angle. The relatively sediment-free portion of the sample 350 flows into the neck 360 of the bottle 110. This allows the needle 150 to be shorter since shorter needles will not draw from the lower portion of the suspension which contains the sediment of resin/culture medium 370. When the bottle is oriented in the manner illustrated in FIG. 10B, the second bevel 320 is oriented facing upward to further control the aspiration of suspended resin beads. For drawing (i.e. by aspiration) sample from the culture bottle, the angle of the bottle neck 360 from horizontal is about 9.5 degrees to about 20 degrees. These orientations of culture bottle 200 are illustrated in FIG. 11A (9.5°), 11B (12.5°), and 11C (20°).

Figure 12:
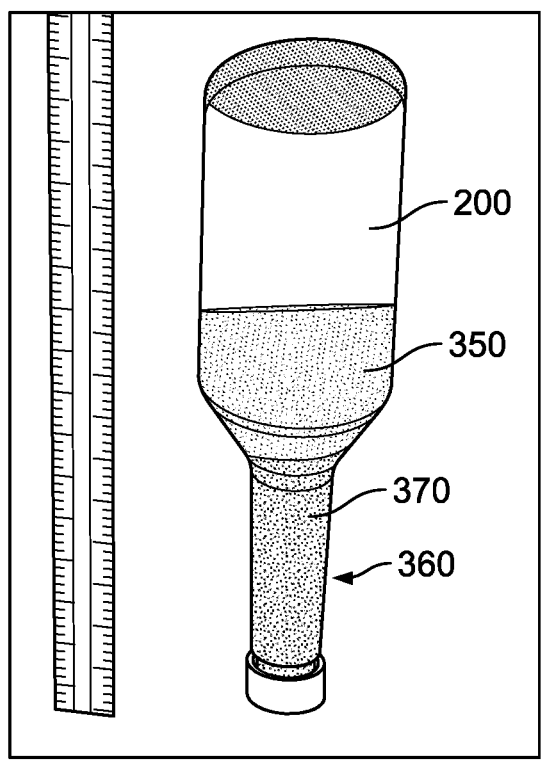
FIG. 12 illustrates an inverted blood culture bottle, showing the relative amounts of culture media and solution and the relative volume of headspace.

FIG. 12 illustrates the culture bottle 200 upside down orientation (180-degree rotation). A wait time of about 30 seconds is needed to allow resin/culture medium 370 to settle into the neck 360 of the culture bottle 200 (i.e. resin fills neck approximately 57 mm deep). At this point the aliquot needle (150 in FIG. 10B) can be inserted about 65 mm inside the culture bottle to bypass the resin/culture medium 370 and collect sample from the relatively sediment-free portion of the sample 350. In this embodiment, an aliquot needle with a length of about 100 mm is required to reach the relatively sediment-free portion of the sample 350.

Figure 13A:
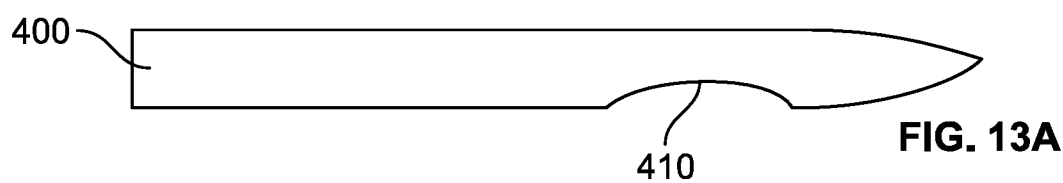
FIG. 13A-D illustrated different venting needle configurations.
Figure 13B:
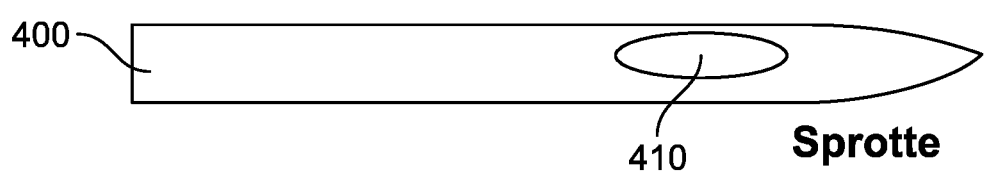
Figure 13C:
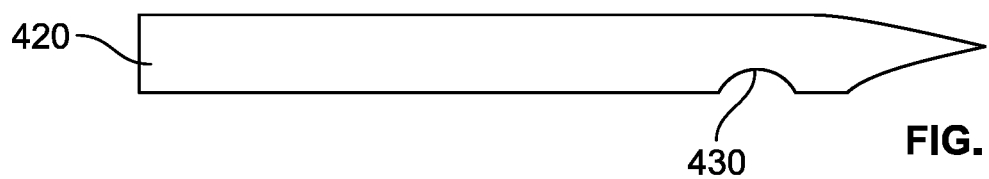
Figure 13D:
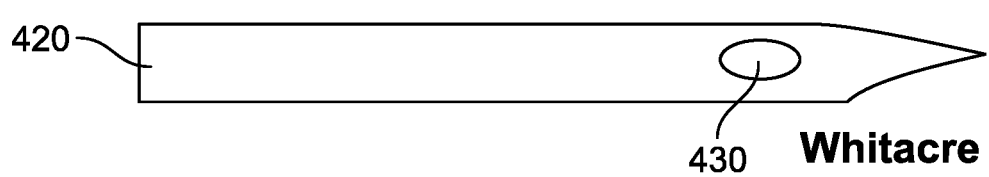

FIG. 13A-D illustrates different optional needle types that can be used as the aliquot needle 150 described herein. FIG. 13A-B illustrate a Sprotte needle 400 with the needle opening 410 in side view (FIG. 13A) and in top view (FIG. 13B). FIG. 13 C-D illustrate a Whitacre needle 420 with the needle opening 430 in side view (FIG. 13C) and in top view (FIG. 13D).

Figure 14:
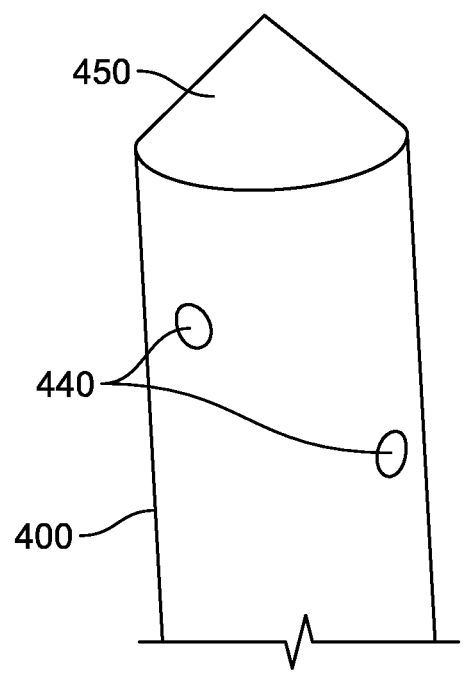
FIG. 14 is a detail view of one venting needle configuration.

FIG. 14 illustrates another optional needle design which has a plurality of openings 440 on the side of the needle/cannula. Optionally the needle is a sidepencil pointed needle. The size of the openings 440 can optionally be controlled to be smaller than the resin beads in the culture media. The number of openings 440 can also be controlled. Typically, such needles have a closed pencil point tip 450 and typically a single side hole 440 to aspirate fluid into a collection container (not shown). Examples of other needle point styles includes Pencan® (a registered trademark of B. Braun Medical Inc.) and Gertie Marx needles. These needle designs are well known to one skilled in the art and are not described in detail herein. These types of needles are typically used for spinal applications can be manufactured in small sizes down to 25 gauge (0.515 mm). Optionally, the needles described herein are about 20 gauge. Optionally, the needles illustrated in FIGS. 13A-D can have multiple openings.

For the embodiment illustrated in FIG. 14, the single pencil tip point design has a hole 440 size of about 0.15 mm. Since the bead size diameter is about 0.2 mm to about 0.6 mm, so that resin from the sample/culture medium does not enter the openings 440 of the single pencil tip point design. The needle geometries described herein are contemplated as suitable for piercing the septum of the culture bottle 200 and the collection vessel 220.

Because the needles 140 and 150 are held within the housing 110, the user of the device is protected from incidental contact with the sharp points of the needles 140 and 150. Optionally, the needles 140, 150 are coated with butyl rubber sleeves to further protect a user from inadvertent puncture.

Optionally, the disposable device described herein is used in an automated process. In such process, the sequence of which is illustrated in FIG. 3, venting with needle 140 occurs before the first port 120 is fully advanced on the neck 360 of the culture bottle 200. After the needle 140 has vented the culture bottle 200, the culture bottle 200 is slowly rotated end over end. After the bottle 200 is tilted to about 45 degrees, rotation is paused for about 30 seconds to allow the resin beads/culture media 370 to settle in corner of the culture bottle 200.

Rotation is then re-continued to the predetermined aliquot angle. In this example, the aliquot angle is about 20 degrees. The disposable device is then further advanced onto the neck 360 of the culture bottle so that the aliquot needle 150 penetrates the cap 220 (i.e. septum) of the culture bottle 200. Upon this second penetration, fluid flows from the culture bottle 200 to the collection tube 210. After collection, the collection tube 210 is removed from the disposable device 100. The culture bottle 200 is then removed from the disposable device. The user then disposes of the disposable device in a manner consistent with medical waste with sharps embedded therein.

Figure 15:
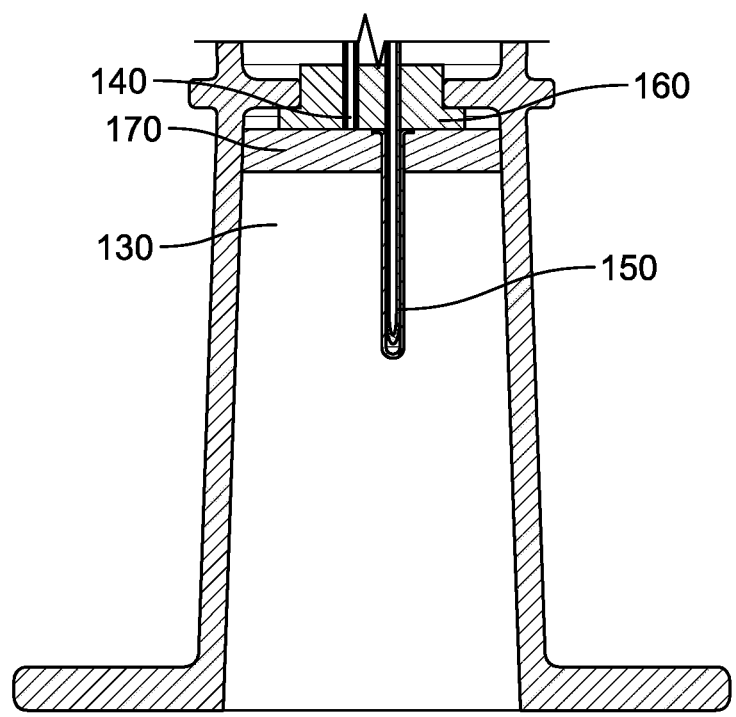
FIG. 15 is a detailed cross-section of the second port of the disposable apparatus that connects with the collection vessel.

FIG. 15 is a detailed cross-section of the second port 130 of the disposable apparatus 100. The venting needle 140 terminates in the needle insert 160 that connects with the collection vessel (not shown). The antimicrobial foam layer 170 is positioned adjacent to the needle insert 160 at the distal end of the port 130. The aliquoting needle 150 is in fluid communication with both the illustrated second port and the first port 120 (FIG. 17).

Figure 16:
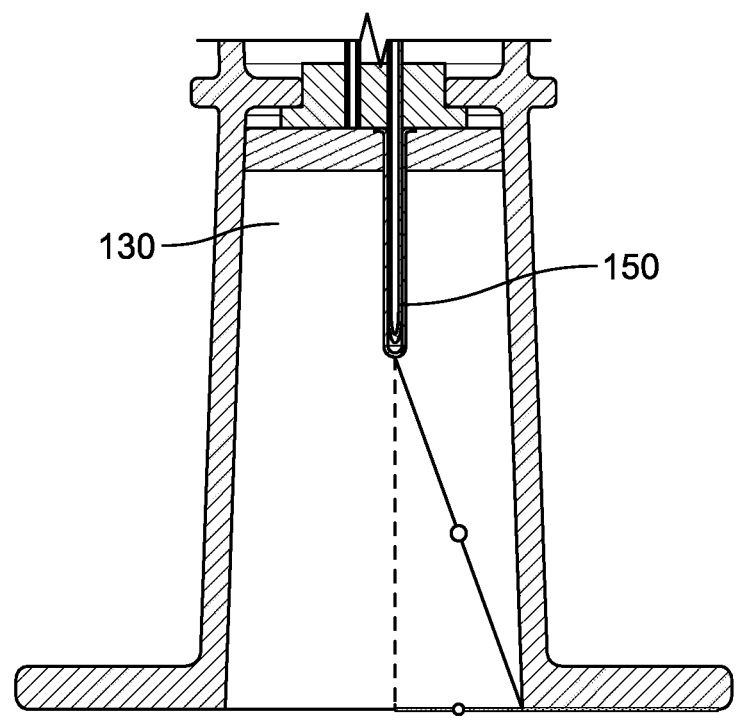
FIG. 16 is the cross-section of FIG. 15 illustrating a placement of the aliquot needle from the side of the disposable apparatus.

FIG. 16 is the cross-section of FIG. 15 illustrating a placement of the aliquot needle 150 from the side of the second port 130 in the disposable apparatus. The aliquoting needle 150 is illustrated as having a bevel such as those described above, which reduces the hazards of handling sharps.

Figure 17:
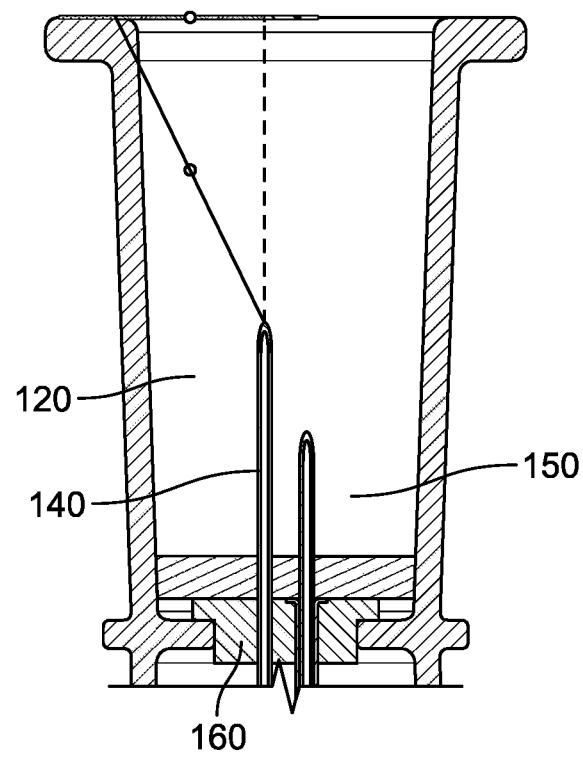
FIG. 17 is the cross-section of the first port of the disposable apparatus, illustrating a placement of the aliquoting needle from the side of the disposable apparatus.

FIG. 17 is a cross-section of the first port 120 of the disposable apparatus, illustrating a placement of the venting needle 140 from the side of the first port 120 of the disposable apparatus. The needles are retained in the device by needle insert 160. As described above disposable foam is provided to absorb any aerosol that is vented from the culture bottle during venting. The difference in length of the two needles (140, 150) that extend into the first port 120 and the rate at which the dual port disposable device is advanced into contact with the culture vessel 200 determines the length of time that the culture vessel 200 is vented. Also, the length difference between the venting needle and the aliquot needle is sufficient to allow automation equipment to perform the following steps:
1. make the first penetration (venting);
2. stop the penetration;
3. rotate the culture vessel;
4. wait for bead settling;
5. rotate bottle to optimal aliquot angle;
6. continue plunge to second penetration (in position to commence aliquot);
7. aliquot;
8. disassemble collection vessel and culture bottle from the disposable device; and
9. safely dispose of disposable device.

The molded housing may be made of the following materials: i) polypropylene (PP); or ii) injection moldable blends including, but not limited to polypropylene (PP), polycarbonate (PC), acrylonitrile butadiene styrene (ABS), polyethylene (PE), polystyrene (PS), Nylon, and Acetal. The needles 140, 150 are optionally either 304 stainless steel, 316 stainless steel, Inconel 625, or Nitinol. The end of the venting needle 140 is that terminates in the foam optionally has an aluminum crimp on the needle barrel, a flared end an adhesive fillet, or an interference fit to retain the needle in the insert. The aliquot needle is fixed in the devices using one of an aluminum crimp on the barrel or an adhesive fillet. The antibacterial agent used in foam is optionally bleach, ammonia-based, alcohol-based, hydrogen peroxide, or an antimicrobial gel. Examples of foam material include, but are not limited to low density polyurethane, open cell wood pulp, or sodium sulphate hemp fiber composite. Any or all of the three needle points optionally have butyl rubber sleeves to further protect the needles from contaminants. Optionally, such a sleeve is only over the aliquot needle side.

In an alternate embodiment, the culture bottle 200 is held in an upright position for both venting and aliquoting. In some situations, this orientation is preferable such as when the samples are thick or viscous and therefor have the potential to clog the aliquoting needle if inverted. In such embodiments, at least the aliquoting needle is much longer and, optionally, but the aliquoting needle and the venting needle are longer. Optionally, in these embodiments, both the aliquoting needle and the venting needle may be 100 mm long or longer.

Figure 19:
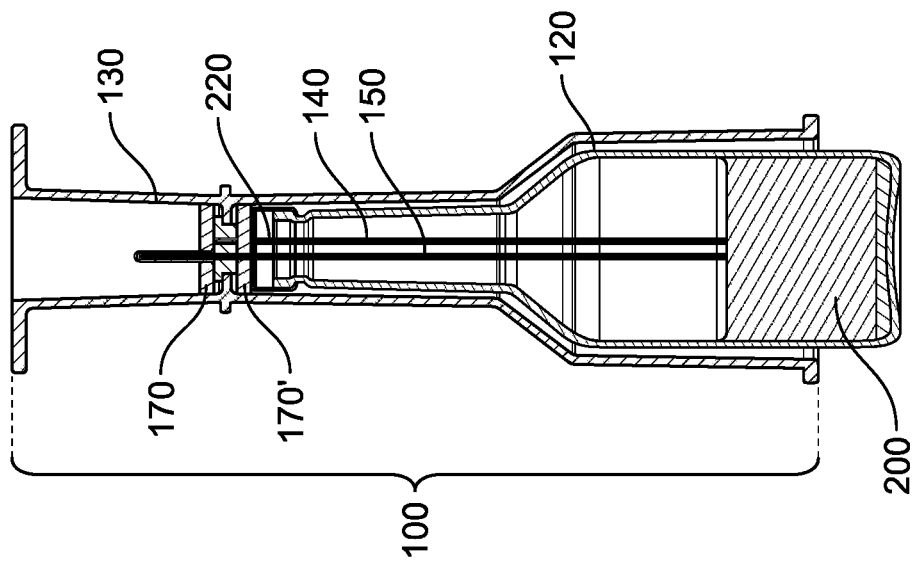
FIG. 19 is a cross-section of the disposable device of FIG. 18 where the device is positioned for aliquoting in the upright position.
Figure 18:
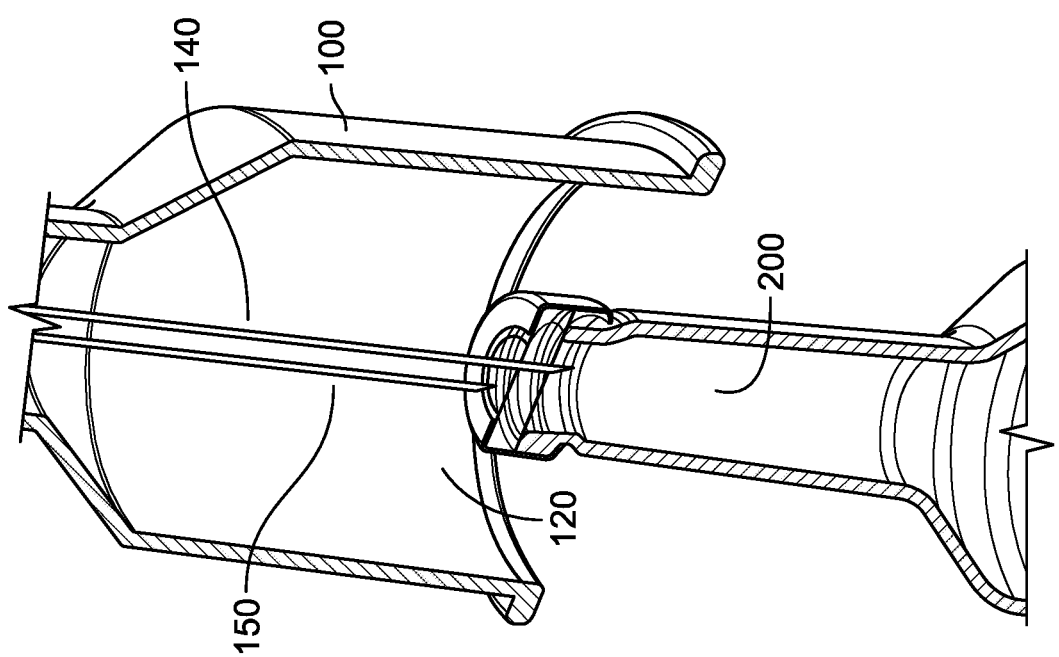
FIG. 18 is cross section of the disposable device in an alternative embodiment where the culture bottle is aliquoted in an upright position.

Referring to FIG. 18, as in other embodiments, the culture bottle 200 is received by the first port 120 of the dual port device 100. The dual port device has venting needle 140 and aliquoting needle 150. Referring to FIG. 19, the venting needle 140 and the aliquoting needle 150 are substantially longer than in the previous illustrated embodiments. The dual port device 100 is advanced onto the neck of the culture bottle 200 until the cap 220 of the culture bottle is at the distal end of the first port 120. Also, in the embodiment illustrated in FIG. 19, microbial foam layer 170, 170' is placed at both the distal end of the first port 120 and the distal end of the second port 130.

Figure 20:
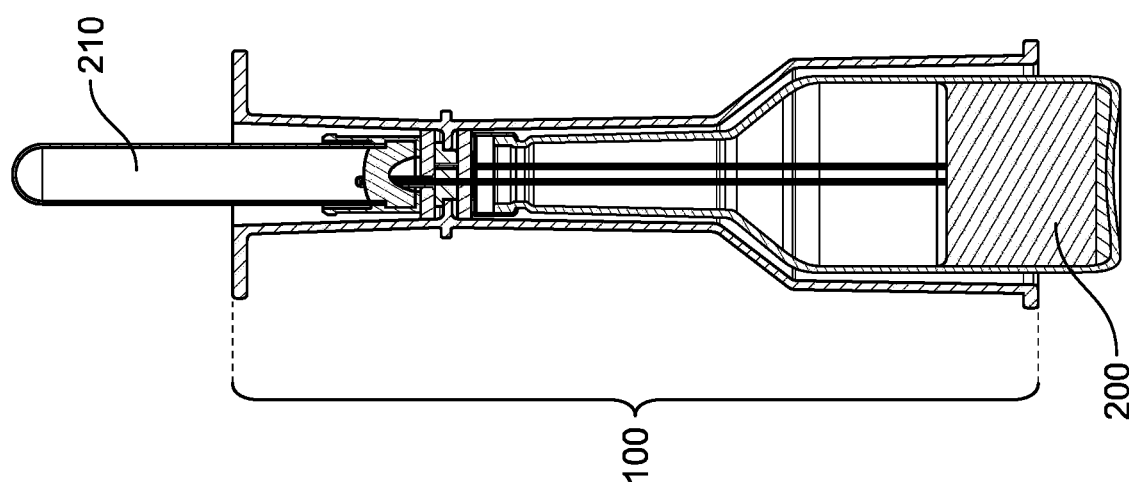
FIG. 20 is a cross-section of the disposable device of FIG. 19 wherein the collection vessel is in fluid engagement with the culture bottle via the disposable device.

Referring to FIG. 20, after the dual port device 100 has been advanced to the aliquoting position on the culture bottle 200 as illustrated in FIG. 19, the collection vessel 210 is inserted into the second port 130 of the dual port device 100. In these configurations, the length of aliquoting needle is sufficient to reach into the sample, but will not reach into the portion of the sample having the settled sediment of culture medium/resin. Therefore, the order of puncture of the culture bottle is the same as in the prior embodiments. That is the venting needle pierces the culture bottle cap/septum first, after which the culture bottle cap/septum is pierced by the aliquoting needle. After the culture bottle cap/septum is pierced by the aliquoting needle, the collection vessel (such as a vacutainer) is inserted into the second port of the disposable device. Keeping the bottle and assembly upright in the vertical direction causes the high viscosity/thick consistency mixture of culture media/resin/sample to settle at the bottom of the culture bottle allowing the less viscous, more free-flowing portion of the culture bottle contents to be aliquoted therefrom.

Figure 21:
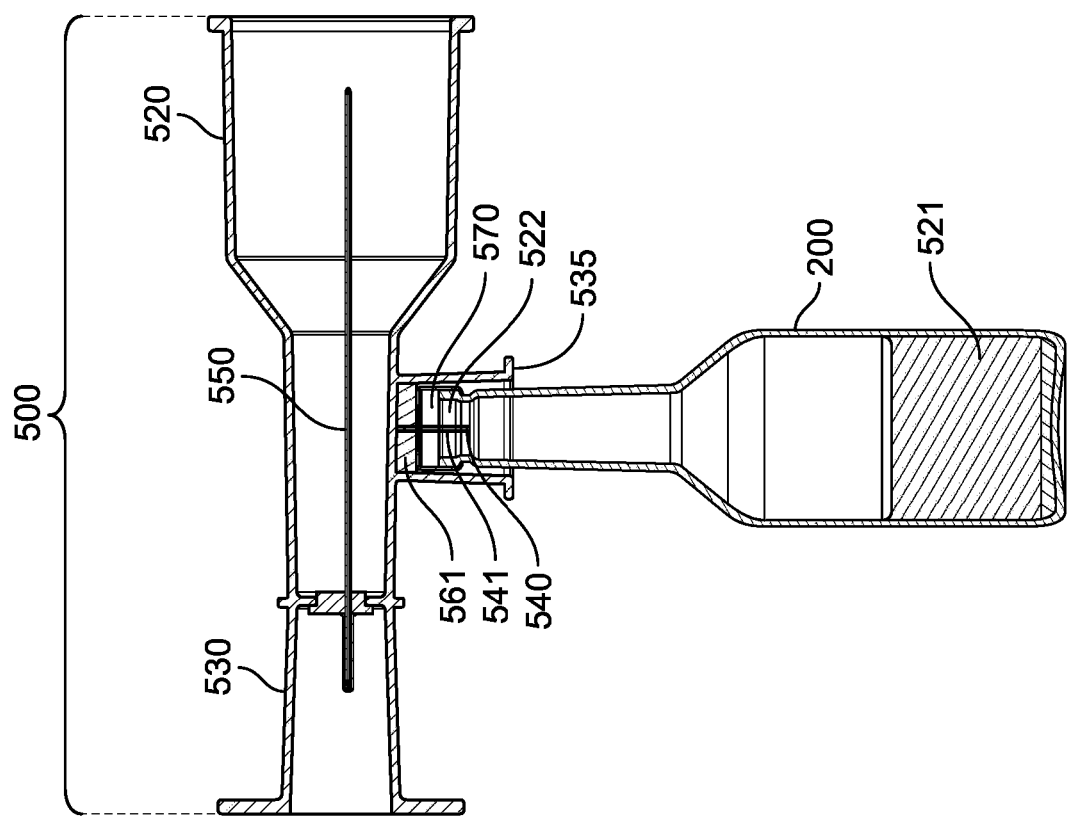
FIG. 21 is a cross-section of a three-port configuration of the disposable device described herein placed on the culture bottle for venting.
Figure 23:
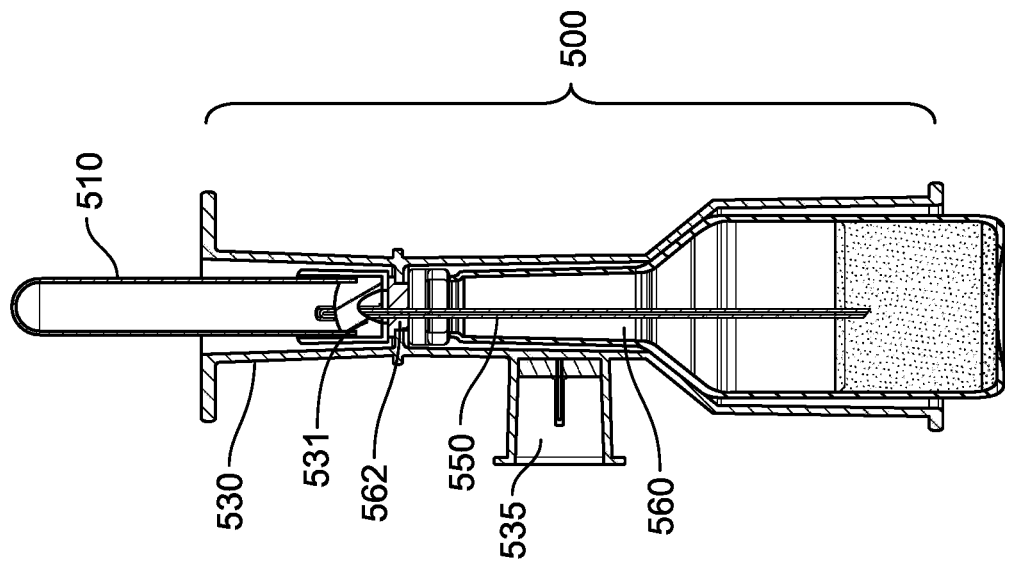
FIG. 23 is a cross-section of the device of FIG. 24 but with the collection vessel place therein.
Figure 22:
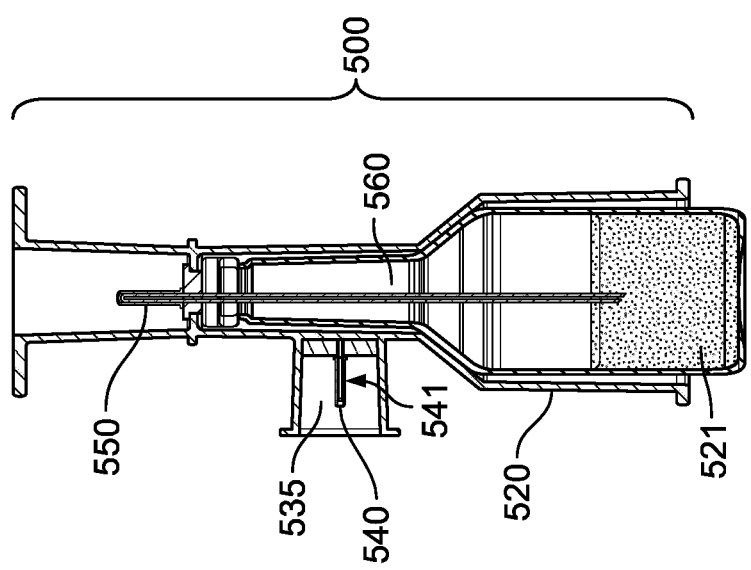
FIG. 22 is a cross-section of the device of FIG. 23 but rotated to the aliquoting position.

Optionally, the disposable device 500 illustrated in FIGS. 21-23 has a third port 535. The third port 535 permits the venting operation to occur with a shorter, less expensive needle 540 that is inserted through the cap 522. The third port 535 has a needle insert 561 and antimicrobial foam layer 570 into which aerosol from the venting needle 540 will be captured. The venting needle 540 has a sleeve 541 that captures any contamination after venting.

In FIG. 22, after venting, the disposable device 500 is removed from engagement with the culture bottle 200, rotated, and the port 520 is seated on the neck 560 of the culture bottle 200. As the port 520 is advanced downward onto the neck 560 of the culture bottle 200, the aliquot needle 550 pierces the cap 520 of the culture bottle 200 and the distal end of the aliquoting needle is advanced into the sample 521. Referring to FIG. 23, after the disposable device 500 has been advanced onto the neck 560 of the bottle 200 such that the cap 520 is adjacent the second needle insert 562, the collection vessel 510 is inserted into the port 530 and the proximal end of the aliquoting needle 550 pierces the septum 531 of the collection vessel 510.

Figure 24:
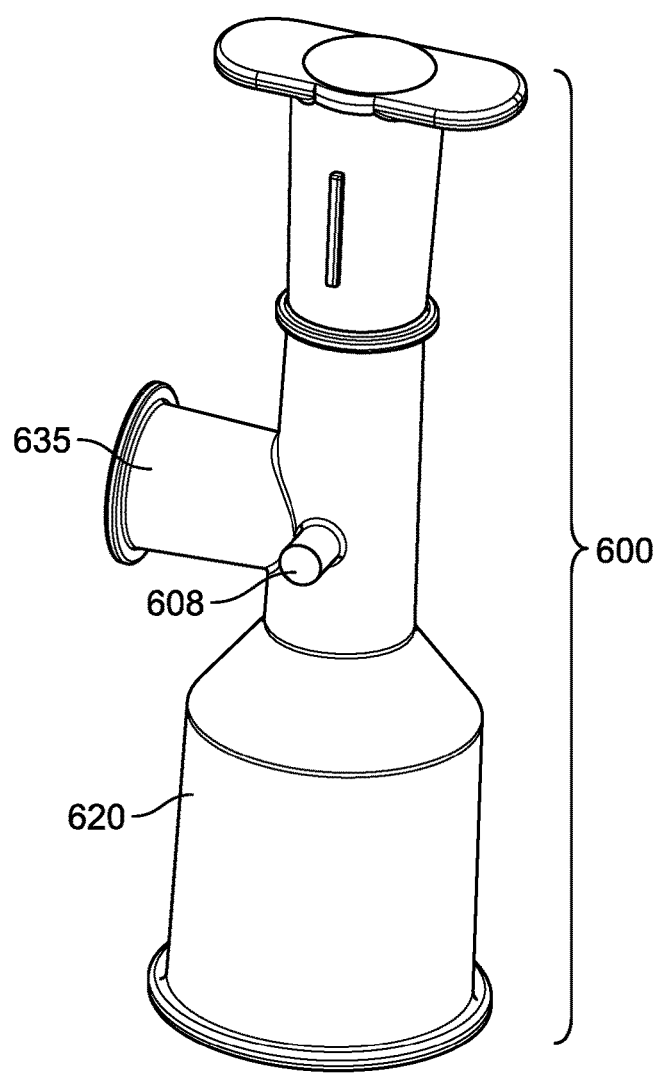
FIG. 24 is a perspective view of the three-port configuration of the disposable device with features for automated handling.

Referring to FIG. 24, optionally, the disposable device 600, which is a slight modification of the disposable device 500 illustrated in FIG. 21-23, has a feature 608 which facilitates automating the rotation of the device 600 when moving the device from the venting orientation to the aliquoting orientation. Optionally, the disposable device 600 is moved but the culture bottle is not. In FIG. 24, the feature 608 is a round knob that can be gripped by a three-finger gripper that can grab device 600 in an orientation where the third port 635 is facing in a direction necessary to receive and engage the culture bottle and, once the culture bottle is vented, remove the port 635 of the disposable device 600 from engagement with the culture bottle, rotate the disposable device 600 and then place port 620 into engagement with the culture bottle such that the aliquoting needle therein pierces the cap of the culture bottle. Since the object is to vent the culture bottle, the culture bottle is positioned with the neck of the culture bottle upward, so that sample in the culture bottle is not in communication with the venting needle.

Figure 25:
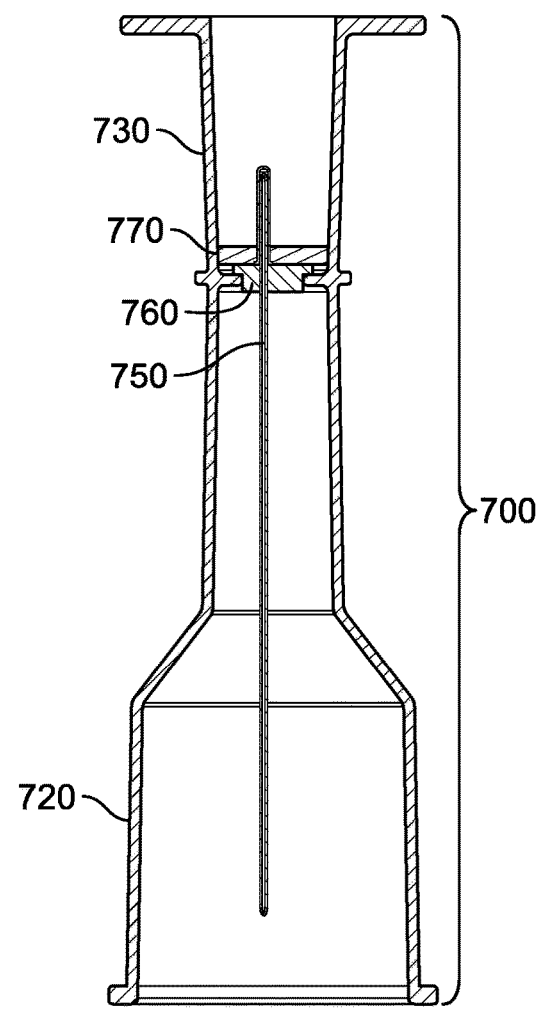
FIG. 25 is a cut-away view of a two-port device with only one needle.

Referring to FIG. 25, aerosolization may occur in a minority of culture bottles being processed and acceptable low level of risk may be assumed to perform aliquots without venting. Optionally, a disposable device that is two chambers but with only one needle 750 is contemplated. The disposable device 700 has first port 720 and second port 730. First port 720 receives the collection bottle (not shown). Second port 730 receives the collection device (not shown). Needle insert 760 has anti-microbial infused foam 770 on the second port 730 side of the needle insert 760 to capture any aerosol that might vent through aliquot needle 750 when it pierces the cap of the culture bottle.

Figure 26:
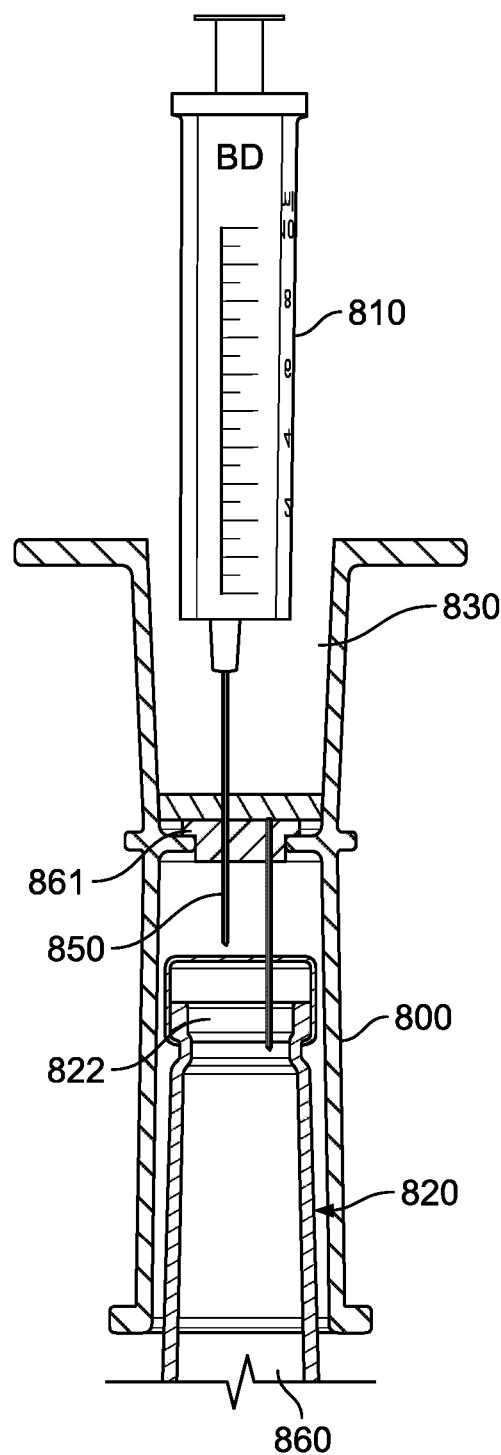
FIG. 26 illustrates the two-port device with a syringe collection device.

FIG. 26 illustrates a disposable device 800 with a collection port 830 adapted to receive a syringe 810 and a port 820 adapted to receive a culture bottle. The culture bottle neck 860 with cap 822 are illustrated in FIG. 26. The aliquoting cannula 850 passes through the needle insert 861. The antimicrobial foam 870 is placed at the distal end of the port 830 that receives the syringe. The aliquoting cannula is in fluid communication with the syringe 810. The syringe 810 is at sub-atmospheric pressure (i.e. a partial or full vacuum) and thereby draws the sample from the culture bottle through the cannula 850. Once the syringe 810 has drawn the aliquot from the culture bottle, the syringe 810 is removed from the device 800 for downstream processing.

Figure 27A:
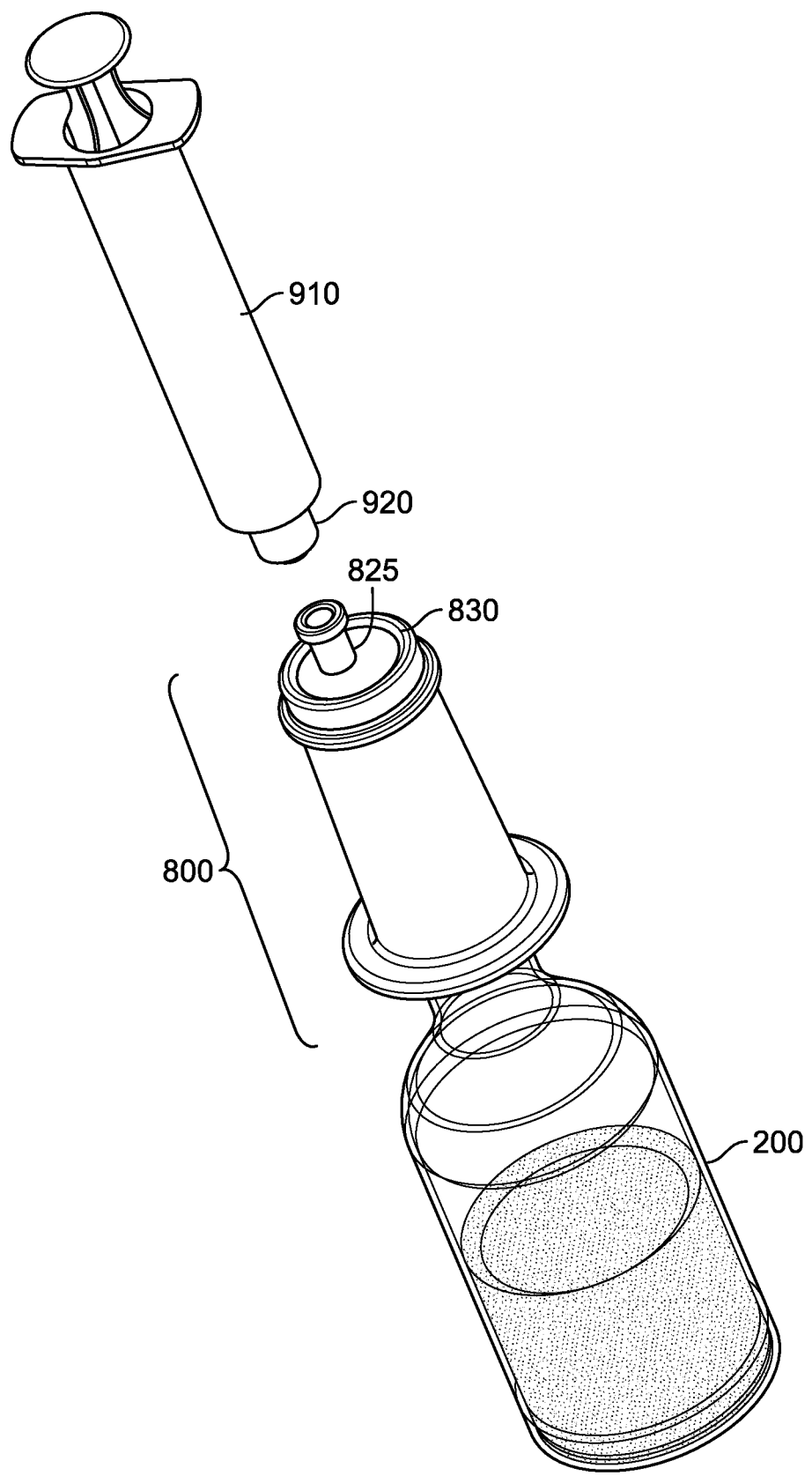

FIG. 27A illustrates the disposable device 800 placed on culture bottle 200 wherein the collection port 830 has a luer lock fitting 825 that will fluidically couple the collection device 910 (illustrated as a needleless syringe with luer connector 911) to the contents of the culture bottle 200. The disposable device has two needles, the venting needle 840 and the aliquoting needle 850. Referring to FIG. 27B, the cannula 850, which provides the flow path from the culture bottle 200 to the collection device 910 terminates at the luer lock 825. The collection device 910 is placed in fluid communication with the cannula 850 and the sample aliquot is drawn. With reference to FIG. 3, the disposable device 800/culture bottle 200/collection device assembly 910 is rotated so that the cannula 850 is in fluid communication with the contents of the culture bottle 200 for aliquoting. Referring to FIG. 27C, thereafter, the collection device 910 is disconnected from the luer connector 825 of the disposable device 800 and the collection device 910 is used to transfer the collected sample for downstream processing.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive.

It will further be understood that any reference herein to subject matter known in the field does not, unless the contrary indication appears, constitute an admission that such subject matter is commonly known by those skilled in the art to which the present technology relates.

The invention claimed is:

1. A multi-port disposable device for venting a sealed sample device and aliquoting therefrom, the device comprising:
   a plurality of ports, wherein a first one of the plurality of ports is a first culture vessel port configured to receive a top portion of a culture vessel, the first culture vessel port having a proximal end that is open to receive the culture vessel and a distal end that terminates at a first culture vessel port needle insert wherein the first culture port needle insert is secured by a flange at the distal end of the first culture vessel port;
   a second one of the plurality of ports is a sample collection vessel port configured to receive a sample collection vessel, the sample collection vessel port having a proximal end that is open to receive the sample collection vessel and a distal end that terminates at a sample collection vessel port needle insert wherein the sample collection vessel port needle insert may be a shared needle insert with the first culture vessel port or a separate needle insert;
   a third one of the plurality of ports that is a second culture vessel port configured to receive the top portion of the culture vessel, the second culture vessel port having a proximal end that is open to receive the culture vessel and a distal end that terminates at a second culture vessel port needle insert;
   a venting needle disposed in the second culture vessel port needle insert of the multi-port disposable device and extending from the second culture vessel port needle insert, the venting needle comprising a cannula that extends therethrough and terminates in the second culture vessel port needle insert; and
   an aliquoting needle with a cannula that extends through the sample collection vessel port needle insert at the distal end of the first culture vessel port and the sample collection vessel port and provides fluid communication between the culture vessel received in the first culture vessel port and the collection vessel received in the sample collection vessel port, the aliquoting needle comprising a proximal end and a distal end, the proximal end configured to pierce a septum or cap of the culture vessel and the distal end configured to pierce a septum or cap of the collection vessel.

2. The multi-port disposable device of claim 1, wherein the multi-port disposable device further comprises a layer of foam carrying a microbial agent disposed adjacent the second culture vessel port needle insert at the distal end of the second culture vessel port.

3. The multi-port disposable device of claim 2, wherein the layer of foam carrying the microbial agent is placed at the distal end of the second culture vessel port and wherein the cannula of the venting needle terminates in the layer of foam.

4. The multi-port disposable device of claim 2, wherein the first culture vessel port needle insert is held in an opening from the distal end of the first culture vessel port to the distal end of the sample collection vessel port.

5. The multi-port disposable device of claim 1, wherein a layer of foam carrying a microbial agent is adjacent the second culture vessel port needle insert.

6. The multi-port disposable device of claim 1, wherein at least one of the venting needle and the aliquoting needle, or both, has a sheath thereon.

7. A multi-port disposable device for venting a sealed sample device and aliquoting therefrom, the device comprising:

a plurality of ports, wherein a culture vessel port is configured to receive a top portion of a culture vessel, the culture vessel port having a proximal end that is open to receive the culture vessel and a distal end that terminates at a culture vessel port needle insert wherein the culture vessel port needle insert is secured by a flange at the distal end of the culture vessel port;

a sample collection vessel port configured to receive a syringe, the sample collection vessel port having a proximal end that is open to receive the syringe and a distal end that terminates at the culture vessel port needle insert;

a venting needle disposed in the culture vessel port needle insert and extending from the culture vessel port needle insert, the venting needle comprising a cannula that extends from the culture vessel port needle insert and into the sample collection vessel port and terminates in the culture vessel port needle insert; and an aliquoting needle with a cannula that extends from the syringe through the culture vessel port needle insert and provides fluid communication between the culture vessel received in the culture vessel port and the syringe received in the sample collection vessel port, the aliquoting needle comprising a proximal end and a distal end, the proximal end configured to pierce a septum or cap of the culture vessel.

8. The multi-port disposable device of claim 7, wherein the sample collection vessel port is a connector adapted to connect to the syringe and having proximal and distal ends corresponding to the proximal and distal ends of the sample collection port, the connector in fluid communication with the aliquoting needle, wherein the proximal end of the connector fluidically connects with the syringe and the distal end of the connector fluidically connects to the aliquoting needle.

9. The multi-port disposable device of claim 8, wherein the connector is a luer connector.

10. The multi-port disposable device of claim 9, wherein the cannula of the aliquoting needle extends from the connector that receives and connects to the syringe in the sample collection vessel port.

11. The multi-port disposable device of claim 7, wherein the aliquoting needle is carried by the syringe into the multi-port device.

* * * * *